US00PP33062P3

(12) United States Plant Patent
van Sambeek

(10) Patent No.: US PP33,062 P3
(45) Date of Patent: May 11, 2021

(54) ***PENSTEMON* PLANT NAMED 'DOPENSPRISLIPUR'**

(50) Latin Name: *Penstemon barbatus*
Varietal Denomination: Dopensprislipur

(71) Applicant: DUMMEN GROUP B.V., De Lier (NL)

(72) Inventor: Ellen van Sambeek, Oegstgeest (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 16/501,823

(22) Filed: Jun. 11, 2019

(65) Prior Publication Data

US 2020/0396884 P1 Dec. 17, 2020

(51) Int. Cl.

| | |
|---|---|
| ***A01H 5/02*** | (2018.01) |
| ***A01H 6/00*** | (2018.01) |
| ***A01H 6/68*** | (2018.01) |

(52) U.S. Cl.
USPC ..... Plt./465
CPC ..... *A01H 6/00* (2018.05); *A01H 5/02* (2013.01); *A01H 6/68* (2018.05)

(58) Field of Classification Search
USPC ..... Plt./465
CPC ..... A01H 6/68
See application file for complete search history.

(56) References Cited

PUBLICATIONS

Dummen Perennial website, *Penstemon* plant, 'Pristine Lilac Purple', 'Dopensprislipur', published May 23, 2018, downloaded from https://issuu.com/bepplersrl/docs/d_mmen_perennials_2018-2019, downloaded Apr. 2, 2020, p. 1, and 30-31.*

* cited by examiner

*Primary Examiner* — Anne Marie Grunberg
(74) *Attorney, Agent, or Firm* — C. Anne Whealy

(57) ABSTRACT

A new and distinct cultivar of *Penstemon* plant named 'Dopensprislipur', characterized by its upright and tall plant habit; vigorous growth habit; freely branching habit; freely flowering habit; long flowering period; deep purple-colored flowers; and good garden performance.

1 Drawing Sheet

Botanical designation: *Penstemon barbatus.*
Cultivar denomination: 'DOPENSPRISLIPUR'.

BACKGROUND OF THE INVENTION

The present invention relates to a new and distinct cultivar of *Penstemon* plant, botanically known as *Penstemon barbatus* and hereinafter referred to by the name 'Dopensprislipur'.

The new *Penstemon* plant is a product of a planned breeding program conducted by the Inventor in Aalsmeer, The Netherlands. The objective of the breeding program was to create new freely-branching *Penstemon* plants with attractive flower color.

The new *Penstemon* plant originated from an open-pollination in July, 2013 in Aalsmeer, The Netherlands, of a proprietary selection of *Penstemon barbatus* identified as code number PE-0010, not patented, as the female, or seed, parent with an unknown selection of *Penstemon barbatus* as the male, or pollen, parent. The new *Penstemon* plant was discovered and selected by the Inventor as a single flowering plant from within the progeny of the stated open-pollination in a controlled environment in Aalsmeer, The Netherlands in May, 2014.

Asexual reproduction of the new *Penstemon* plant by terminal vegetative cuttings in a controlled environment in Aalsmeer, The Netherlands since June, 2014 has shown that the unique features of this new *Penstemon* plant are stable and reproduced true to type in successive generations.

SUMMARY OF THE INVENTION

Plants of the new *Penstemon* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Dopensprislipur'. These characteristics in combination distinguish 'Dopensprislipur' as a new and distinct *Penstemon* plant:

1. Upright and tall plant habit.
2. Vigorous growth habit
3. Freely branching habit.
4. Freely flowering habit.
5. Long flowering period.
6. Deep purple-colored flowers.
7. Good garden performance.

Plants of the new *Penstemon* differ primarily from plants of the female parent selection in branching habit as plants of the new *Penstemon* are more freely branching than plants of the female parent selection.

Plants of the new *Penstemon* can also be compared to plants of *Penstemon schmidel* 'Marble Riding Hood', disclosed in U.S. Plant Pat. No. 23,098. In side-by-side comparisons, plants of the new *Penstemon* and 'Marble Riding Hood' differ in the following characteristics:

1. Plants of the new *Penstemon* are taller than plants of 'Marble Riding Hood'.

2. Plants of the new *Penstemon* are more freely branching than plants of 'Marble Riding Hood'.
3. Plants of the new *Penstemon* have darker green-colored leaves than plants of 'Marble Riding Hood'.
4. Plants of the new *Penstemon* have deep purple-colored flowers whereas plants of 'Marble Riding Hood' have light red purple and white-colored flowers.

BRIEF DESCRIPTION OF THE PHOTOGRAPH

The accompanying colored photograph illustrates the overall appearance of the new *Penstemon* plant showing the colors as true as it is reasonably possible to obtain in colored reproductions of this type. Colors in the photograph may differ slightly from the color values cited in the detailed botanical description which accurately describe the colors of the new *Penstemon* plant.

The photograph is a side perspective view of typical flowering plant of 'Dopensprislipur' grown in a container.

DETAILED BOTANICAL DESCRIPTION

The aforementioned photograph and following observations, measurements and values describe plants grown during the spring in 17-cm containers in a glass-covered greenhouse in Aalsmeer, The Netherlands and under cultural practices typical of commercial *Penstemon* production. During the production of the plants, day temperatures averaged 22° C. and night temperatures averaged 17° C. Plants were pinched one time and were three months old when the photograph was taken and 22 weeks old when the detailed description was taken. In the following description, color references are made to The Royal Horticultural Society Colour Chart, 2007 Edition, except where general terms of ordinary dictionary significance are used.

Botanical classification: *Penstemon barbatus* 'Dopensprislipur'.

Parentage:

*Female, or seed, parent*.—Proprietary selection of *Penstemon barbatus* identified as code number PE-0010, not patented.

*Male, or pollen, parent*.—Unknown proprietary selection of *Penstemon barbatus*, not patented.

Propagation:

*Type*.—By vegetative cuttings.

*Time to initiate roots, summer*.—About 12 days at temperatures about 26° C.

*Time to initiate roots, winter*.—About 16 days at temperatures about 23° C.

*Time to produce a rooted young plant, summer*.—About 16 days at temperatures about 23° C.

*Time to produce a rooted young plant, winter*.—About 20 days at temperatures about 18° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Herbaceous perennial typically grown as a container and garden plant; upright and tall plant habit; vigorous growth habit; rapid growth rate.

*Plant height*.—About 44 cm.

*Plant width (spread)*.—About 38 cm.

*Lateral branches*.—Quantity of lateral branches: Freely branching habit, about eight to nine primary lateral branches develop per plant. Length: About 44 cm. Diameter: About 4 mm. Internode length: About 3 cm to 4 cm. Strength: Strong. Aspect: Upright. Texture: Smooth, glabrous. Color, developing: Close to 145B. Color, developed: Close to 143C.

Leaf description:

*Arrangement*.—Opposite, simple; sessile.

*Length*.—About 21 cm.

*Width*.—About 3.5 cm.

*Shape*.—Lanceolate.

*Apex*.—Acuminate.

*Base*.—Truncate.

*Margin*.—Entire.

*Texture, upper and lower surfaces*.—Smooth, glabrous.

*Venation pattern*.—Pinnate, reticulate.

*Color*.—Developing leaves, upper surface: Close to 137A. Developing leaves, lower surface: Close to 137C. Fully expanded leaves, upper surface: Between darker than 137A and lighter than 139A; venation, close to 143C. Fully expanded leaves, lower surface: Close to 147B; venation, close to 139D.

Flower description:

*Flower shape, arrangement and flowering habit*.—Single bi-labiate flowers arranged on terminal racemes; flowers face mostly outwardly; freely flowering with about 30 flowers developing per inflorescence; about 200 flower buds and about 240 to 270 open flowers developing per plant.

*Fragrance*.—None detected.

*Time to flower*.—Early flowering habit, plants begin to flower about twelve weeks after planting.

*Natural flowering season*.—Long flowering period, plants flower from June to August in The Netherlands; flowers last about two weeks on the plant, flowers not persistent.

*Flower buds*.—Length: About 5 mm to 8 mm. Diameter: About 2 mm to 4 mm. Shape: Elongate ovoid. Texture: Smooth, glabrous. Color: Close to 185C.

*Inflorescence height*.—About 30 cm.

*Inflorescence diameter*.—About 9 cm.

*Flower width (horizontal)*.—About 1 cm to 2 cm.

*Flower length (vertical)*.—About 2 cm to 2.5 cm.

*Flower depth*.—About 3 cm to 3.5 cm.

*Petals*.—Arrangement: Five, fused into a tube; bilabiate, upper lip with two upper petals and lower lip with three lower petals. Length, upper and lower lips: About 1 cm. Width, upper and lower lips: About 7 mm. Shape: Oval to rounded. Apex: Obtuse. Margin: Entire; not undulate. Texture, upper and lower surfaces: Smooth, glabrous; proximally, sparsely pubescent. Color: When opening, upper and lower surfaces: Close to 83B. Fully opened, upper surface: Close to 83B; venation, close to 83B; color does not change with development. Fully opened, lower surface: Close to 83B; venation, proximally, close to 71A and distally, close to 83B; color does not change with development.

*Sepals*.—Arrangement: Five sepals fused in a single whorl. Length: About 8 mm. Width: About 2 mm. Shape: Ovate. Apex: Acuminate. Margin: Entire. Texture, upper and lower surfaces: Smooth, glabrous. Color: Developing and fully developed, upper surface: Close to 143A. Developing and fully developed, lower surface: Close to 143A.

*Peduncles*.—Length: About 44 cm. Diameter: About 4 mm. Aspect: Upright. Strength: Strong. Texture: Smooth, glabrous. Color: Close to 143C.

*Pedicels*.—Length: About 1.5 cm to 2 cm. Diameter: About 1 mm. Strength: Strong. Texture: Smooth, glabrous. Color: Close to 143C.

*Reproductive organs*.—Stamens: Quantity per flower: Four. Filament length: About 2 cm to 2.7 cm. Filament color: Close to 155D. Anther size: About 3 mm by 1 mm. Anther shape: Oval to rounded. Anther color: Close to 159B. Pollen amount: Moderate. Pollen color: Close to 155C. Pistils: Quantity per flower: One. Pistil length: About 2 cm to 2.3 cm. Style length: About 2 cm to 2.2 cm. Style color: Close to 155D. Stigma diameter: About 1 mm. Stigma shape: Cylindrical. Stigma color: Close to 155D. Ovary color: Close to 144C.

*Seeds and fruits*.—To date, seed and fruit development have not been observed on plants of the new *Penstemon*.

Garden performance: Plants of the new *Penstemon* have been observed to have good garden performance and tolerate rain, wind and temperatures ranging from −5° C. to 30° C.

Pathogen & pest resistance: To date, plants of the new *Penstemon* have not been observed to be resistant to pathogens and pests common to *Penstemon* plants.

It is claimed:

1. A new and distinct *Penstemon* plant named 'Dopensprislipur' as illustrated and described.

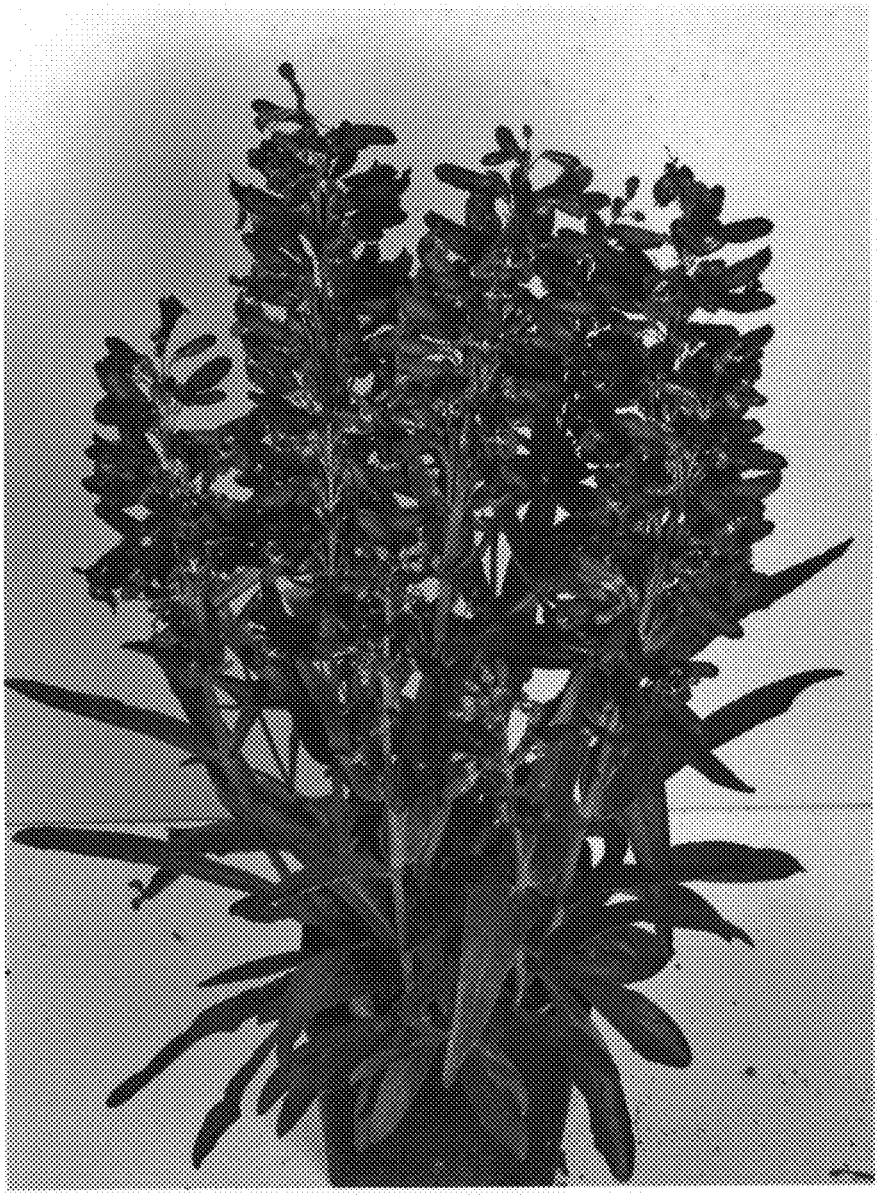

* * * * *